United States Patent [19]

Pietsch et al.

[11] Patent Number: 4,778,461
[45] Date of Patent: Oct. 18, 1988

[54] HEART VALVE PROSTHESIS AND PROCESS FOR ITS PRODUCTION

[75] Inventors: Hanns Pietsch; Holger Kartheus; Hans-Joachim Holtzmann, all of Hamburg; Günther Sachau, Quickborn; Helmut Reul, Düren, all of Fed. Rep. of Germany

[73] Assignee: Beiersdorf AG, Hamburg, Fed. Rep. of Germany

[21] Appl. No.: 931,755

[22] Filed: Nov. 17, 1986

[30] Foreign Application Priority Data

Nov. 23, 1985 [DE] Fed. Rep. of Germany ....... 3541478

[51] Int. Cl.$^4$ ............................................. A61F 2/24
[52] U.S. Cl. ...................................... 623/2; 623/900
[58] Field of Search .................................. 623/2, 900

[56] References Cited

U.S. PATENT DOCUMENTS

| | | | |
|---|---|---|---|
| 4,035,849 | 7/1977 | Angell | 623/2 |
| 4,259,753 | 4/1981 | Liotta | 623/2 |
| 4,265,694 | 5/1981 | Bovetos | 623/2 |
| 4,490,859 | 1/1985 | Black | 623/2 |
| 4,605,407 | 8/1986 | Black | 623/2 |

Primary Examiner—Ronald L. Frinks
Assistant Examiner—James Prizant
Attorney, Agent, or Firm—Sprung Horn Kramer & Woods

[57] ABSTRACT

A heart valve prosthesis for replacing the aortic valve or the pulmonary valve, consisting of a support ring with at least two commissure supports in each case and flexible cusps, is characterized in that the height of the support ring including the commissure supports is less than the total height of the heart valve prosthesis.

15 Claims, 3 Drawing Sheets

$$F(x) = \frac{a_0}{2} + \sum_{K=1}^{K=\infty} \left\{ \left[ \frac{2}{\ddot{U}_1} \cdot \int_0^{\ddot{U}_1} \left( \frac{hst}{2} \cdot \cos(x) + \frac{hst}{2} \right) \cdot \cos(K \cdot w_0 \cdot x) \cdot dx \right] \right.$$

$$+ \left[ \frac{2}{\ddot{U}_1} \cdot \int_0^{\ddot{U}_1} \left( \frac{hst}{2} \cdot \cos(x) + \frac{hst}{2} \right) \cdot \sin(K \cdot w_0 \cdot x) \cdot dx \right]$$

$$+ \left[ \frac{2}{\ddot{U}_2 - \ddot{U}_1} \cdot \int_{\ddot{U}_1}^{\ddot{U}_2} \left( r_3 - \sqrt{r_3^2 - r_2^2 - r_1^2 + 2 \cdot r_2 \cdot r_1 \cdot \cos\left(\frac{\delta \cdot \pi}{180}\right)} \right) \cdot \cos(K \cdot w_0 \cdot x) \cdot dx \right]$$

$$+ \left[ \frac{2}{\ddot{U}_2 - \ddot{U}_1} \cdot \int_{\ddot{U}_1}^{\ddot{U}_2} \left( r_3 - \sqrt{r_3^2 - r_2^2 - r_1^2 + 2 \cdot r_2 \cdot r_1 \cdot \cos\left(\frac{\delta \cdot \pi}{180}\right)} \right) \cdot \sin(K \cdot w_0 \cdot x) \cdot dx \right]$$

$$+ \left[ \frac{2}{T_0 - \ddot{U}_2} \cdot \int_{\ddot{U}_2}^{T_0} \left( \frac{hst}{2} \cdot \cos(x) + \frac{hst}{2} \right) \cdot \cos(K \cdot w_0 \cdot x) \cdot dx \right]$$

$$+ \left. \left[ \frac{2}{T_0 - \ddot{U}_2} \cdot \int_{\ddot{U}_2}^{T_0} \left( \frac{hst}{2} \cdot \cos(x) + \frac{hst}{2} \right) \cdot \sin(K \cdot w_0 \cdot x) \cdot dx \right] \right\}$$

$\ddot{U}_1$ = TRANSITION POINT 1
$\ddot{U}_2$ = TRANSITION POINT 2
$T_0$ = PERIOD LENGTH = SUPPORT RING CIRCUMFERENCE / 3
$hst$ = MAXIMUM SUPPORT RING HEIGHT
$w_0 = 2 \cdot \pi / T_0$
$r_1$ = EXTERNAL RADIUS OF SUPPORT RING
$r_2$ = CENTRE RADIUS OF SUPPORT RING
$r_3$ = SPHERICAL CONSTRUCTION RADIUS
$\delta$ = CONSTRUCTION ANGLE
$K$ = SERIAL VARIABLE
$X$ = POSITION ON THE DEVELOPED VIEW OF THE SUPPORT RING $0 \leq x \leq$ SUPPORT RING CIRCUMFERENCE / 3
$a_0$ = RADIUS-DEPENDENT AUXILIARY PARAMETER FOR CONSTRUCTION

FIG. 4

HEART VALVE PROSTHESIS AND PROCESS FOR ITS PRODUCTION

BACKGROUND OF THE INVENTION

1. Field of the Invention

The invention relates to a heart valve prosthesis consisting of a support ring with at least two, preferably three, commissure supports and flexible (or semilunar) cusps, and to preferred processes for producing them. Such prostheses are used for the replacement of aortic valves or pulmonary valves on human hearts.

2. Background Information

In recent years, a number of cusp valve prostheses have already been disclosed, wherein attempts were made by means to the most diverse design forms to imitate the natural aortic valve or pulmonary valve as closely as possible with respect to function and structure. For example, German Patent Specification No. 2,355,959 describes a semilunar valve for replacing the aortic valve or pulmonary valve, which has the essential structural feature that it is so flexible in its cross-section that it is able to follow the changes in size and cross-section of the base of the aortic valve or pulmonary valve. Although such a highly flexible system has certain advantages, it has the technical functional disadvantage that, in the event of excessive stretching, the cusps can flap over. Moreover, it is difficult to fix the textile suture ring, by means of which the prosthesis is fastened to the heart, to a support ring of such flexibility.

A very important disadvantage of this and other known heart valves is, however, above all that the height of the commissure support is equal to the height of the cusp valves, so that the forces arising during the opening and closing movement of the cusps are applied particularly to the tips of the commissure supports and can cause cracking at these stressed points.

SUMMARY OF THE INVENTION

It was therefore the object of the invention to develop a heart valve of the type set out above, which avoids this weak point of the known prosthetic heart valves. In addition, its outline should be shaped such that it does not have any points of attack for blood depositions, thrombi or scleroses and can be reproduced with high accuracy by allowing the use of machines, computer-controlled if possible, in preparation of the molds. It was a further object of the invention to establish the most suitable materials for the preparation of the cusps and the support ring, and to develop an improved process for producing them.

The first-mentioned object is achieved by a heart valve prosthesis for replacing the aortic valve or the pulmonary valve, which prosthesis consists of a support ring with at least two commissure supports in each case and flexible cusps and which is characterized in that the height of the support ring including the commissure supports is less than the total height of the heart valve prosthesis. Preferably, the said height amounts to 20–80%, particularly advantageously 40–60%, of the total height.

This means that the support ring, which preferably consists of a plastic material which is particularly deformable elastically, supports only the lower part of the valve, whereas the upper part of the cusps and their joining zones (the commissures) remain free and flexible. This has the result that the forces which arise on movement of the heart valve and are concentrated at the tips of the commissures, can be distributed harmonically over the free height of the cusp joints, and only a fraction of the forces is applied directly to the support ring.

In order to optimize the flow-dynamic properties of the heart valve, in addition to a longer life, a further feature essential to the invention is that all the construction lines and surfaces of the valve are formed by straight lines, circles, planes and spheres, the transitions of which are adapted by rounding radii, so that all edges, corners and transitions are rounded, in such a way that the mathematical functions underlying these construction lines are steady and fully differentiable.

The equation for calculating the curved upper edge of the support ring according to FIG. 2, following this criterion, is reproduced hereinbelow. Such mathematic equations and functions can be calculated by a person skilled in the art and can also be stored as a working program in computer-controlled machine tools which prepare the molds for producing the heart valve parts.

DETAILED DESCRIPTION OF THE INVENTION

The further preferred features of the heart valve prosthesis according to the invention are that the prosthesis has three flexible, inwardly curved cusps, similar to the human aortic valve, and correspondingly three commissure supports, the boundary edges of the cusps in plan view showing the outline of a symmetrical three-pointed star, the rays of which each consist of two adjacent, mutually parallel boundary edges. These boundary edges are located on an imaginary spherical surface, in such a way that the point of interception of the three pairs of edges is at the lowest point. Moreover, the boundary edges of the cusps are thickened and rounded in such a way that they have a lobar shape in cross-section. As a result, they have a particularly low flow resistance for the blood stream and a high tear resistance.

Depending on the Shore hardness and breaking strength of the flexible material used for the cusps, the wall thickness of the latter can be 50–1000 micrometers.

In accordance with the general constructional features indicated, according to which all the transitions are rounded, the lower, inner transition of the cusps on the support ring edge is also rounded, and this has an advantageous effect on the stability and load-bearing capacity of this line which is subject to high stress.

Since the commissure supports of the heart valve support ring do not reach, according to the invention, as far as the upper edge of the commissures (joints) between the cusps, their upper region consists of the cusp material. Advantageously, the commissures are reinforced in this region, that is to say the material is thickened here, whereby the heart valve is mechanically stabilized and is protected against flapping over of the cusps.

Figure 2:
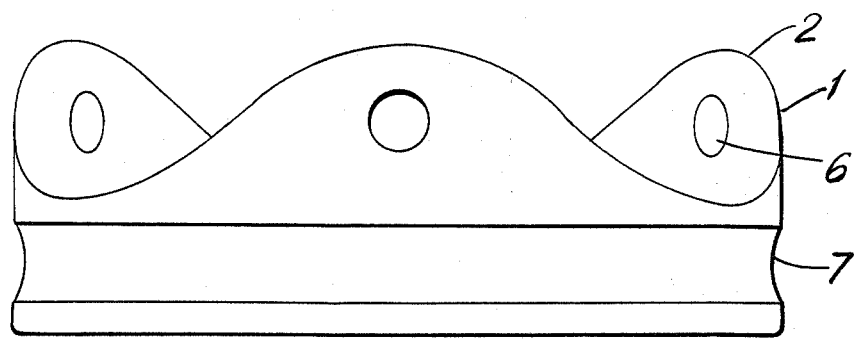
FIG. 2 is an elevation side view of the support ring of the heart valve as depicted in FIG. 1.

The support ring (or "stent"), such as is shown in FIG. 2, as an example, and which is designed for three cusps, is a ring having a plane lower edge and a curved upper edge as well as an all-round groove for fixing the suture ring. The curved edge has three points of maximum height, namely the commissure supports, and three points of minimum height, which are each arranged radially symmetrically at an angle of 120°. The all-round groove and all the edges are again rounded, with the exception of the lower inner edge resting planely. In the region of each of the three highest points, there is preferably an orifice, which is used above all for fixing the ring on the machine during the production of the heart valve.

The function of the support ring is to provide support to the flexible cusps and thus to prevent flapping over of the valve and to make provision for anchoring the suture ring.

For suturing the heart valve in the heart, the conventional textile suture rings can be used, which preferably consist of tubular woven or knitted fabrics of cotton, polyester or nylon fibres and are extensible in the radial direction. A suture ring of a polyester (polyethylene glycol terephthalate) fabric having a deflection temperature under load of up to at least 150° C. and a radial extensibility of at least 10% is particularly suitable. Depending on the use of the heart valve, different suture rings are used, above all the three "subanular", "supraanular" or "aortic" versions. The suture ring can be fixed in the groove of the support ring by means of sewing, preferably by glueing.

A further preferred feature, which above all contributes to the longest possible life of the heart valve according to the invention without thrombosis or sclerosis, is that the support ring and the cusps are formed integrally as a result of the plastic skin, from which the cusps are formed, also enclosing the support ring. The groove on the support ring, in which the suture ring is fixed, may here be excepted. This produces a heart valve which is "all of one piece".

In order to achieve this, it was necessary to develop a particularly suitable process for producing the prosthesis and to establish the materials which are most suitable.

The most diverse products can be used as the material for producing the support ring, provided that they are physiologically acceptable and are not degraded by the body. Examples of these are stainless steel, titanium, niobium, tantalum, aluminium, vitreous carbon, fused silica, soda-lime glass, sintered calcium phosphate ceramics, sintered titanium dioxide ceramics, sintered zirconium dioxide ceramics or thermoplastics such as polyethylene glycol terephthalate (polyester), polyethersulphone, polycarbonate, polyurethane, polyethylene or polypropylene having a deflection temperature under Load above 150° C., preferably between 150° and 250° C.

However, polyamides which can contain short glass fibres for reinforcement up to 50% of their weight have proved to be a particularly suitable material. Nylon 6,6 with 15% of glass fibres, which is preferred, can be processed by injection-molding and is sufficiently heat-resistant to withstand the necessary temperatures of 180°-200° C. for brief periods. In addition, it has outstanding mechanical properties, namely: yield stress (according to DIN 53 455) greater than 60 N/mm$^2$, elongation at break (according to DIN 53 455) less than 100%, modulus of elasticity (according to DIN 53 457) greater than 3000 N/mm$^2$, density (according to DIN 53 497) greater than 1, 1 g/m$^2$, moisture absorption (according to DIN 53 479) less than 3%, water absorption at 23° C. (according to DIN 53 495) less than 9% and deflection temperature under load (according to ISO 75, method A) above 150° C.

Hitherto, linear, uncrosslinked polyether-urethanes obtained from difunctional isocyanates, alcohols and amines, have preferably been used for flexible heart valves, these are processed either by the dipping process or the deep-drawing process. These urethanes are commercially available, usually dissolved in dimethylformamide, dimethylacetamide or dioxane/tetrahydrofuran mixtures, as 10-30% solutions.

It has been found in animal experiments, however, that they are not fully resistant to enzymatic and/or hydrolytic degradation in the organism. The reason may be that the amide bonds —NH—CO— present in the polyurethanes are comparable with the peptide bonds present in proteins.

According to the invention, this problem is solved by the flexible cusps consisting of a three-dimensionally crosslinked polymer material which is insoluble in both water and organic solvents. The important point here is that the material has a low Shore A hardness of 20-80 coupled with a high breaking strength.

Crosslinked polyether-urethanes which have a so-called interpenetrating network (IPN) have proved particularly suitable for this purpose. They have the advantage that, for producing the cusps by the dipping process, an uncrosslinked solution of the polymers can be used and the crosslinking takes place, after the film has dried, by treatment with water.

The polyether-urethanes used are preferably segmented polyether-urethanes such as are described, for example, in U.S. Pat. No. 2,929,804. These polyurethanes have properties which are very highly compatible with blood, but they are degradable in the tissue. However, by adding γ-aminopropyltrisethoxysilane or the corresponding trimethoxy compound, the polyether-urethanes can be post-crosslinked. The result of crosslinking is that they become insoluble in dimethylacetamide, in which the uncrosslinked urethane is soluble when cold. In addition, isopropyl myristate can be added as a lubricant to the solution, in order to obtain better flow on dipping. A preferred mixture consists of 96% of urethane, which has has been freed from sizes and impurities by repeated rinsing in ethyl acetate, 3% of isopropyl myristate and 1% of γ-aminopropyltrisethoxysilane. After the cross-linking reaction, such polyurethanes have a Shore A hardness of 60-80. When this material is used in the dipping process, the wall thickness of the cusps is 80-200 micro-meters.

Another particularly suitable material is silicone rubber, which crosslinks at high temperature (=HTV) and is used in the preferred form of a two-component liquid rubber (liquid silicone rubber=LSR). Such silicone rubbers have a high compatibility with blood and a high fatigue strength in alternate bending as well as a high breaking strength at a low Shore A hardness. After crosslinking, the preferred silicone rubbers have Shore A hardnesses in the range of 25-60, preferably 25-35, a breaking strength of at least 8 N/mm$^2$, a tensile strength of more than 8 MPa (according to DIN 53 504) and an elongation at break of more than 400%.

They can be processed by injection-moulding, and their extremely favourable flow properties with a viscosity of less than $2.10^6$ mPa.s makes it possible to use extremely small cross-sections for gates and runners when building the mould. Since these silicone rubbers, when still uncrosslinked, are also soluble in organic solvents such as hexane, octane etc., gasoline, toluene or xylene, they can also be processed in the dipping process, like the polyurethanes.

The rubbers are formed by the reaction of two linear polydimethylsiloxane components, one component containing free vinyl groups and the other containing Si—H groups. When coming together, these two groups react with one another in the manner of an addition reaction and thus bond and crosslink the two components. Organic platinum compounds are used as the catalyst for the reaction which proceeds under the action of theat.

To improve the mechanical properties, up to about 25% of surface-active silica can be added to such silicone rubbers.

Instead of the silicone rubbers which have to be processed as a liquid, highly viscous two-component silicone rubbers can also be used. These must be premixed in the extruder and are equivalent in their mechanical properties, but processing is more expensive.

It was the object of the production process for the heart valve prostheses according to the invention to carry out the greatest possible number of production steps by machine and also fully automatically. The following production sequence—listed by keywords—meets these conditions:

1. Production of the support ring by injection-moulding
2. Cleaning of the support ring by removing dust particles, greases, etc.
3. Adhesion-promoting pretreament (chemically and/or physically) or the support ring and, if appropriate, application of an adhesion-promoting coating
4. If appropriate, single or repeated dip-coating of the support ring with the cusp material
5. Production of the flexible cusp part by dip-coating or injection-molding with simultaneous molding to the support ring and coating (enveloping) of the support ring with the cusp material. Crosslinking of the cusp material.
6. Fixing of the textile suture ring
7. Sterilization of the heart valve
8. Packaging under sterile conditions.

Explanation of the individual part steps:

As already described, the support ring should preferably consist of thermoplastics. These can be processed very well by the injection-molding process. Compared with the so-called "chip-removing" shaping techniques, injection-molding has the advantage of very accurate reproducibility, if the mold has been produced with corresponding accuracy and the process parameters are carefully monitored and maintained.

Of course, the support ring can also be produced by other processes, but these represent a deterioration as compared with injection-molding.

Attrition particles, traces of lubricants etc. may be present on the support ring from the production process. These are removed preferably by a two-stage washing process. The first washing process is carried out with water and detergent, and the second is carried out with an organic solvent or solvent mixture. For this purpose, the known organic solvents are suitable, inter alia, such as acetone, ethyl acetate, ethanol, isopropanol, trichlorethylene or gasoline. The preferred surface-active substances are anionic compounds such as sodium laurylsulfonate.

After drying, the cleaned support ring is advantageously pretreated in order to obtain better adhesion of the cusp material. The nature of the treatment depends on the materials of which the support ring and the cusps consist. For a combination in which the support ring consists of nylon 6,6 with 15% of glass fibres and the cusps consist of polyurethane, it is sufficient to etch the nylon incipiently with formic acid and to wash with acetone. When this support ring is combined with cusps of polydimethylsiloxane as the flexible material, an adhesion-promoting coating is carried out after etching. It is important that the adhesion of the flexible material to the support ring in the finished heart valve is greater than the breaking strength of this material—that is to say the adhesion is greater than the cohesion—so that, in an extreme case, it will break rather than become detached from the support ring.

According to the invention, the process for the production of the novel heart valve prosthesis by the dip-coating process with a cusp material of polyurethane, that is to say above all from the polyether-urethanes described, is carried out in such a way that the washed, etched and rinsed support ring is dipped several times into a polyurethane solution (solvent: dimethylacetamide) containing a crosslinking agent and, in between, is dried each time to such an extent that the film no longer flows. The γ-aminopropyltrisethoxy-(or trimethoxy)-silane already mentioned is the preferred suitable crosslinking agent. When a coating of 30–50 micrometers thickness has been reached, which as a rule requires 3–5 dipping steps (depending on the viscosity and concentration of the solution), the ring is pushed over a dip mould which precisely fits the cusps and which is machined such that the three cusps with commissures are formed integrally, and the entire workpiece is then subjected to further dipping steps until the desired film thickness of the cusps of 80–200 micrometers has been reached. This requires another 8–20 dipping steps, depending on the concentration and viscosity of the solution.

In order to obtain a uniform layer thickness, drying is carried out with continuous rotation. In order to keep the surface smooth and dust-free, the work is carried out under dust-free laminar airflow conditions, the laminar flow being preheated, the air temperature being 50°–60° C. and the relative humidity being less than 25%. Drying between the individual dipping steps is controlled such that the urethane no longer flows and the new layer incipiently swells, but no longer destroys the old layer. This is accomplished by not completely removing the solvent, but only to an extent of 95% each time. After the desired layer thickness has been reached, final drying is carried out for 24 hours at 80° C, the product is then removed from the mould and, subsequently, crosslinking is carried out for 100 hours in distilled or deionized water at 80° C., solvent residues and other soluble auxiliaries being extracted simultaneously.

When the flexible part is produced in this manner, the shaping of the bead-shaped boundaries of the cusp edges is carried out by "fusion-cutting" either with a heated wire or a laser beam.

This process for the production of the heart valve prosthesis advantageously differs from that described in German Patent Specification No. 3,248,560 in that, inter alia, the support ring is first dipped alone and thus coated on all sides before it is pushed over the dip mold for the the cusps and is further coated together with the latter. This results in a particularly smooth transition from the support ring to the cusps. Moreover, a solid and homogeneous bond in the coating is produced by the only incomplete drying of the polymer films between the individual dipping steps.

The process for the production of the heart valve prosthesis with cusps of silicone rubber by the reaction-injection-mounting process (liquid silicone rubber=LSR injection-moulding) is carried out in such a way that the support ring pretreated with a suitable anchoring layer is placed into the mold and fixed therein by means of pins, the two silicone components are fed via a metering unit into a mixing tube (static mixer), mixed therein bubble-free with the catalyst and, if appropriate, further additives such as silica and are then injected via a needle nozzle into the mold. Vulcanization then takes place in the mold for 10 minutes at 180° C. Lower temperatures can be used if the reaction time is correspondingly extended, but the reaction temperature must not fall below a minimum of 80° C., if the mechanical properties are not to be impaired.

In order to ensure reproducible fabrication and to meet good manufacturing practice (GMP), the temperature and pressure inside the mold should be monitored and recorded during the vulcanization period and a nominal/actual comparison should be carried out continuously. A precondition for such a process is an injection mold with a fabrication tolerance of 7-3 micrometers and a peak-valley height of 5-3 micrometers. Moreover, the mold-parting planes must be outside the direction of blood flow.

This injection mold is designed such that enveloping of the support ring with the silicone rubber layer also takes place simultaneously during injection-molding in addition to the formation of the cusps. The rounded boundary edges of the cusps are produced in this process by appropriate shaping.

After the production of the heart valve, the suture ring is fixed to the prosthesis in the usual way by sewing and/or glueing into the all-round groove in the support ring.

The heat valve prostheses according to the invention, which are distinguished by their special shaping, the materials preferably used and a matching optimized production, show a particularly favorable rheological behavior, high mechanical stability and fatigue strength as well as good compatibility with blood.

Figure 1:
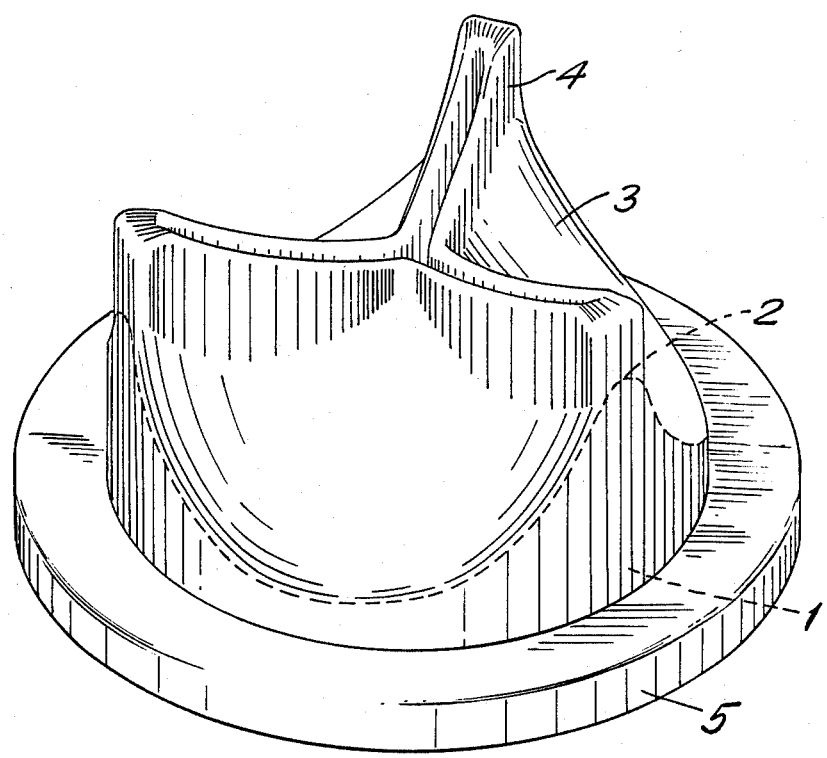
FIG. 1 is a perspective view of a heart valve according to the present invention.

The heat valve prosthesis is explained below by way of example by reference to the drawings in which:

FIG. 1 shows a perspective view of the heart valve according to the invention with the support ring 1, the commissure supports 2, the three cusps 3, the cusp boundary edges 4 and the suture ring 5. The support ring is here indicated only by broken lines, since it is not exposed but is coated with the flexible cusp material.

FIG. 2 shows the free support ring 1 with the commissure supports 2, the orifices 6 and the all-round groove 7 for fixing of the suture ring.

Figure 3:
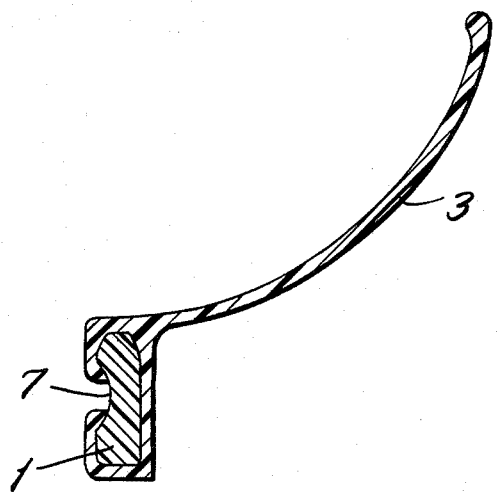
FIG. 3 is a partial cross-sectional view of the heart valve as depicted in FIG. 1.

FIG. 3 shows a partial cross-section through the heart valve with a cusp 3, the support ring 1 and the groove 7. This shows in particular how the cusp material encloses the support ring, and the fact that the boundary edge of the cusp shown has a rounded, lobar thickened outline.

An equation for calculating the upper edge of the support ring is as follows:

$$F(x) = \frac{a_0}{2} + \sum_{K=1}^{K=\infty} \left\{ \left[ \frac{2}{U_1} \cdot \int_0^{U_1} \left( \frac{h_{st}}{2} \cdot \cos(x) + \frac{h_{st}}{2} \right) \cdot \cos(K \cdot \omega_0 \cdot x) \cdot dx \right] + \right.$$

$$\left[ \frac{2}{U_1} \cdot \int_0^{U_1} \left( \frac{h_{st}}{2} \cdot \cos(x) + \frac{h_{st}}{2} \right) \cdot \sin(K \cdot \omega_0 \cdot x) \cdot dx \right] +$$

$$\left[ \frac{2}{U_2 - U_1} \cdot \int_{U_1}^{U_2} \left( r_3 - \sqrt{r_3^2 - r_2^2 - r_1^2 + 2 \cdot r_2 \cdot r_1 \cdot \cos\left(\frac{\delta \cdot \pi}{180}\right)} \right) \cdot \cos(K \cdot \omega_0 \cdot x) \cdot dx \right] +$$

$$\left[ \frac{2}{U_2 - U_1} \cdot \int_{U_1}^{U_2} \left( r_3 - \sqrt{r_3^2 - r_2^2 - r_1^2 + 2 \cdot r_2 \cdot r_1 \cdot \cos\left(\frac{\delta \cdot \pi}{180}\right)} \right) \cdot \sin(K \cdot \omega_0 \cdot x) \cdot dx \right] +$$

$$\left[ \frac{2}{T_0 - U_2} \cdot \int_{U_2}^{T_0} \left( \frac{h_{st}}{2} \cdot \cos(x) + \frac{h_{st}}{2} \right) \cdot \cos(K \cdot \omega_0 \cdot x) \cdot dx \right] +$$

$$\left. \left[ \frac{2}{T_0 - U_2} \cdot \int_{U_2}^{T_0} \left( \frac{h_{st}}{2} \cdot \cos(x) + \frac{h_{st}}{2} \right) \cdot \sin(K \cdot \omega_0 \cdot x) \cdot dx \right] \right\}$$

$Ü_1$ = Transition point 1
$Ü_2$ = Transition point 2
$T_0$ = Period length = support ring circumference/3
$h_{st}$ = Maximum support ring height
$\omega_0 = 2 \cdot \pi / T_0$
$r_1$ = External radius of support ring $r_2$ = Centre radius of support ring
$r_3$ = Spherical construction radius
$\delta$ = Construction angle
$K$ = Serial variable
$x$ = Position on the developed view of the support ring $0 \leq x \leq$ support ring circumference/3
$a_0$ = Radius-dependent auxiliary parameter for construction It will be appreciated that the instant specification and claims are set forth by way of illustration and not limitation, and that various modifications and changes may be made without departing from the spirit and scope of the present invention.

What is claimed is:

1. A heart valve prosthesis for replacing the aortic valve or pulmonary valve, comprising at least two flexible cusps having an upper edge boundary at an upper portion of the heart valve prosthesis with a highest point, and a support ring with at least two commissure supports at an upper portion of the ring and said commissures having an upper edge boundary with a highest point, and wherein the height of the highest point of the commissure supports is 20 to 80% of the height of the highest point of the cusps.

2. A heart valve prosthesis according to claim 1, wherein the height of the support ring including the commissure supports is 40 to 60 of the total height of the heart valve prosthesis.

3. A heart valve prosthesis according to claim 1, wherein all construction lines and surfaces are formed by straight lines, circles, planes and spheres, the transitions of which are adapted by rounding radii, so that all edges, corners and transitions are rounded, in such a way that the mathematical functions underlying these construction lines are steady and fully differentiable.

4. A heart valve prosthesis according to claim 1, wherein the valve has three flexible, inwardly curved cusps and three commissure supports, and the boundary edges of the cusps in plan view show the outline of a symmetrical three-pointed star, the rays of which each comprise two adjacent, mutually parallel boundary edges.

5. A heart valve prosthesis according to claim 1, wherein the boundary edges of the cusps are located on an imaginary spherical surface, in such a way that the point of intersection of the three pairs of cusp edges is at the lowest point.

6. A heart valve prosthesis according to claim 1, wherein the boundary edges of the cusps are rounded and have a lobar outline in cross-section.

7. A heart valve prosthesis according to claim 1, wherein the support ring and the cusps are formed integrally as a result of the plastic skin, from which the cusps are formed, also enclosing the support ring.

8. A heart valve prosthesis according to claim 1, wherein the support ring is composed of a material selected from the group consisting of stainless steel, titanium, niobium, tantalum, aluminium, vitreous carbon, fused silica, silicate glass, sintered calcium phosphate ceramics, sintered titanium dioxide ceramics, sintered zirconium dioxide ceramics and a thermoplastic, the deflection temperature of which under load is above 150° C.

9. A heart valve according to claim 8, wherein the deflection temperature is between 150° and 250° C.

10. A heart valve prosthesis according to claim 8, wherein the support ring is composed of a material selected from the group consisting of nylon 6, nylon 6,6, nylon 6,10, nylon 12, polyethylene glycol terephthalate (polyester), polyether-sulfone, polyoxymethylene, polyurethane, and polycarbonate.

11. A heart valve prosthesis according to claim 10, wherein the support ring contains up to 50% by weight of glass fibers.

12. A heart valve prosthesis according to claim 10, wherein the support ring comprises nylon 6,6 with 15% by weight of glass fibres.

13. A heart valve prosthesis according to claim 1, wherein the cusps comprise a three-dimensionally crosslinked flexible material which is insoluble in all organic solvents and in water and has a Shore A hardness of 20-80.

14. A hear valve prosthesis according to claim 13, wherein the cusps comprise an insoluble polyether-urethane crosslinked with $\gamma$-aminopropyltris-alkoxysilane and having a Shore A hardness of 60-80.

15. A heart valve prosthesis according to claim 13, wherein the cusps comprise a polydimethylsiloxane which has been three-dimensionally crosslinked at high temperature and which can contain up to 25% of active silica and has a Shore A hardness of 25-60 and a minimum breaking strength of 8 N/mm².

* * * * *

UNITED STATES PATENT AND TRADEMARK OFFICE
CERTIFICATE OF CORRECTION

PATENT NO. : 4,778,461

DATED : October 18, 1988

INVENTOR(S) : Hanns Pietsch, et al

It is certified that error appears in the above-identified patent and that said Letters Patent is hereby corrected as shown below:

| | |
|---|---|
| Col. 5, line 15 | Delete "theat" and substitute --heat-- |
| Col. 7, line 10 | Delete "injection-mounting" and substitute --injection moulding-- |
| Col. 8, lines 7, 13 | Before "valve" delete "heat" and substitute --heart-- |
| Col. 8, lines 35-64 | In each instance delete "U" and substitute --Ü-- |
| Col. 9, line 6 | Delete "$0 \leq x \leq$" and substitute --$\emptyset \leq x \leq$-- |
| Col. 10, line 38 | Delete "hear" and substitute --heart-- |

Signed and Sealed this

Twenty-second Day of August, 1989

Attest:

DONALD J. QUIGG

Attesting Officer

Commissioner of Patents and Trademarks